US010327635B2

(12) United States Patent
Huang et al.

(10) Patent No.: US 10,327,635 B2
(45) Date of Patent: Jun. 25, 2019

(54) SYSTEMS AND METHODS TO COMPENSATE FOR REFLECTANCE VARIATION IN OCT ANGIOGRAPHY

(71) Applicant: Oregon Health & Science University, Portland, OR (US)

(72) Inventors: David Huang, Portland, OR (US); Yali Jia, Portland, OR (US); Simon Gao, Portland, OR (US)

(73) Assignee: Oregon Health & Science University, Portland, OR (US)

( * ) Notice: Subject to any disclaimer, the term of this patent is extended or adjusted under 35 U.S.C. 154(b) by 17 days.

(21) Appl. No.: 15/585,089

(22) Filed: May 2, 2017

(65) Prior Publication Data
US 2017/0319060 A1 Nov. 9, 2017

Related U.S. Application Data

(60) Provisional application No. 62/331,316, filed on May 3, 2016.

(51) Int. Cl.
*A61B 3/14* (2006.01)
*A61B 3/00* (2006.01)
*A61B 3/12* (2006.01)
*A61B 3/10* (2006.01)
*G06K 9/62* (2006.01)
*G06K 9/46* (2006.01)

(52) U.S. Cl.
CPC .......... *A61B 3/1233* (2013.01); *A61B 3/0025* (2013.01); *A61B 3/102* (2013.01); *A61B 3/1241* (2013.01); *G06K 9/4604* (2013.01); *G06K 9/6277* (2013.01); *G06K 2209/05* (2013.01)

(58) Field of Classification Search
CPC ..... A61B 3/102; A61B 5/0261; A61B 5/7203; A61B 3/0025; A61B 3/1241; A61B 2576/02; A61B 5/0066; A61B 5/0205; A61B 5/7207; A61B 5/7246; A61B 5/7278; A61B 3/1233; A61B 3/0041; A61B 3/14
USPC ........ 351/200, 205, 206, 209–211, 221, 222, 351/243–246
See application file for complete search history.

(56) References Cited

U.S. PATENT DOCUMENTS

2014/0073917 A1* 3/2014 Huang ................ A61B 5/0066
600/427

* cited by examiner

*Primary Examiner* — Brandi N Thomas
(74) *Attorney, Agent, or Firm* — Schwabe, Williamson & Wyatt, P.C.

(57) ABSTRACT

Methods and systems for improving quantification of OCT angiography data are disclosed. The disclosure specifically relates to methods for compensating for the effect of tissue reflectance to improve the accuracy and repeatability of OCT angiography measurements. These improvements are effected by deriving and then utilizing a dynamic thresholding approach to process decorrelation data to properly classify flow versus non-flow data in OCT angiograms. The disclosed methods overcome quantification errors associated with within-scan variations in reflectance as well as repeatability problems associated with differences in scan quality over successive imaging sessions.

20 Claims, 6 Drawing Sheets

SYSTEMS AND METHODS TO COMPENSATE FOR REFLECTANCE VARIATION IN OCT ANGIOGRAPHY

CROSS REFERENCE TO RELATED APPLICATION

The present application claims priority to U.S. Provisional Patent Application No. 62/331,316, titled "SYSTEMS AND METHODS TO COMPENSATE FOR REFLECTANCE VARIATION IN OCT ANGIOGRAPHY," filed May 3, 2016, the disclosure of which is hereby incorporated by reference in its entirety.

ACKNOWLEDGEMENT OF GOVERNMENT SUPPORT

This invention was made with government support under EY023285, EY024544, DK104397, and EY023211 awarded by the National Institutes of Health. The government has certain rights in the invention.

FIELD

Generally, the field involves methods of using optical coherence tomography (OCT) in angiography. More specifically, the field involves methods to account for reflectance variation to improve quantification in OCT angiography.

BACKGROUND

A number of ocular diseases that result in vision loss are associated with changes in the retinal vasculature. Traditionally, fluorescein and/or indocyanine green angiography have been used to assess these changes, but objective quantification can be challenging with these methods due to dye leakage and/or staining. Optical coherence tomography (OCT) is a noninvasive, depth resolved, volumetric imaging technique that uses principles of interferometry to provide cross-sectional and three-dimensional (3D) imaging of biological tissues. OCT has become part of the standard of care in ophthalmology and is commonly used to visualize retinal morphology. In recent years OCT methods have been extended to allow visualization of blood flow within tissues—an emerging technology termed "OCT angiography." Because OCT angiography does not require the use of injectable dyes, it is not affected by leakage and staining issues and is, thus, more amenable to quantification than dye-based approaches. OCT angiography utilizes variation in the OCT signal on consecutive cross-sectional B-scans at the same location to contrast flowing red blood cells in the vessel lumen from surrounding structural tissue. Because OCT angiography has consistently high contrast for capillary details and is not affected by leakage and staining, quantification is more straightforward than with dye injection methods. By quantifying OCT signal variation between B-scans, for example by calculating decorrelation or speckle variance between images, it is possible to discriminate regions of blood flow (i.e., retinal vasculature) from static tissue and thereby quantify vascular characteristics such as vessel density, vessel area, and avascular area. An efficient OCT angiography algorithm called split-spectrum amplitude-decorrelation angiography (SSADA) has been used in a commercial system to visualize and quantify changes in the vascular networks of the eye.

OCT angiography data is often presented as a projection of the three dimensional dataset onto a single planar image called a 2D en face angiogram. Construction of such an en face angiogram requires the specification of the upper and lower depth extents that enclose the region of interest within the retina to be projected onto the planar image. Once generated, the en face angiogram image may be used to quantify various features of the retinal vasculature, for example, vessel density. This quantification typically involves the setting of a threshold value on the en face angiogram to separate real flow signal in blood vessels from noise, which can arise from bulk tissue motion or from within the OCT system itself. On macular angiograms, the threshold can be based on the average flow signal at a noise region, such as the foveal avascular zone (FAZ), which is known to be free of blood vessels in healthy eyes.

DETAILED DESCRIPTION

Figure 1:
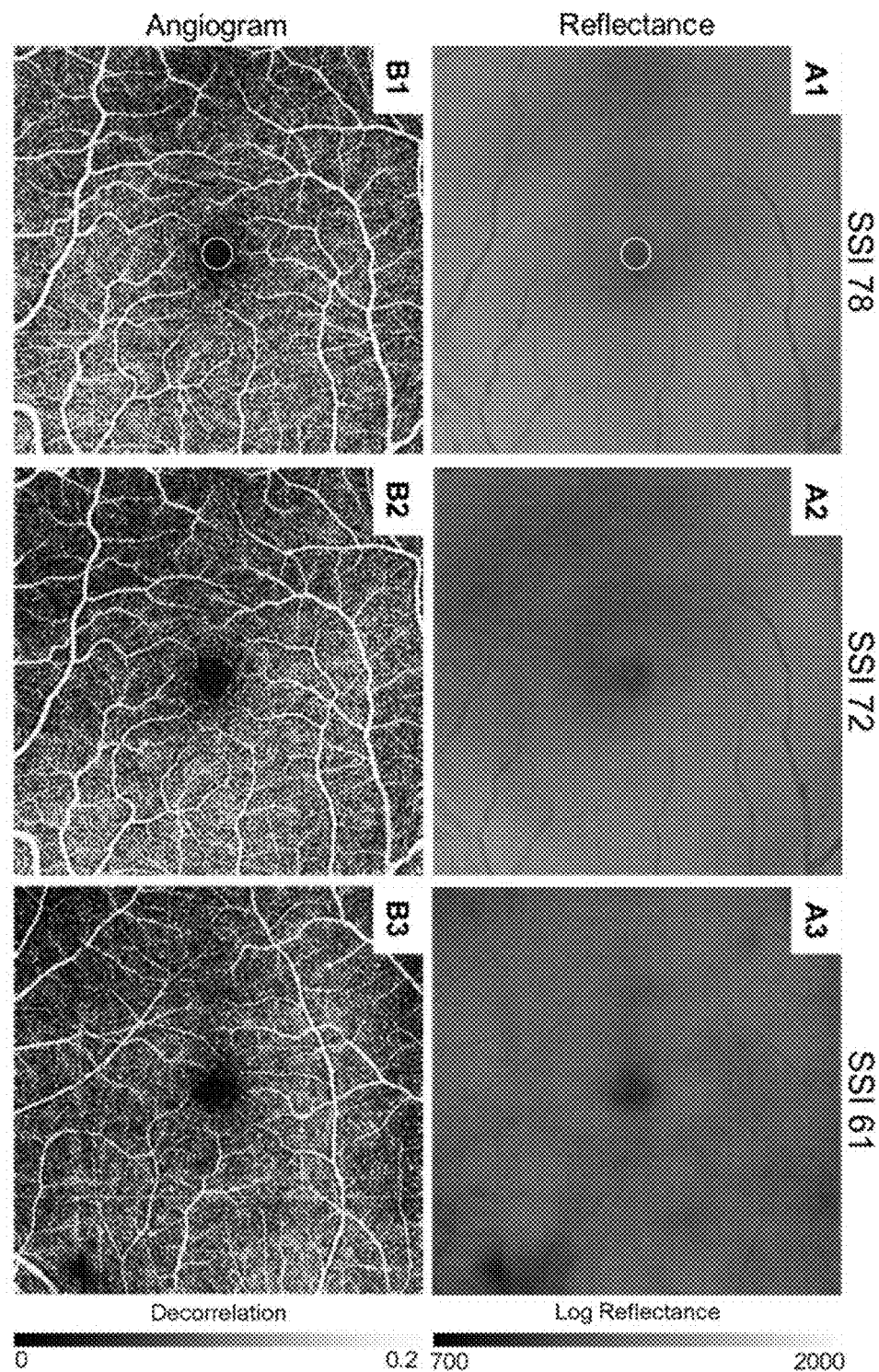
FIG. 1 is a set of en face OCT reflectance images (A1 to A3) and their corresponding respective angiograms (B1 to B3) at three different signal strength index (SSI) values. Reflectance images use the mean projection between the inner limiting membrane (ILM) and outer boundary of inner/outer segment (IS/OS). Angiograms are the maximum decorrelation projection between the same boundaries. The yellow circle identifies the foveal avascular zone. A1, B1 and A2, B2 are from the same participant and A3, B3 is from another participant. Note the regional differences between A1 and A2 despite the images being scanned from the same eye. Scale bars on the right show the range of log reflectance values on an arbitrary scale determined by the RTVue-XR and decorrelation flow signal.

Disclosed herein is a method for use in OCT angiography that increases the accuracy and Disclosed herein is a method for use in OCT angiography that increases the accuracy and repeatability of quantitative measurements of features of the retinal vasculature. A standing problem in both structural OCT and OCT angiography is that the overall signal strength of a given scan (an indicator of scan or image quality) may vary for a given individual both within-visit and over repeated visits separated in time, making comparison of quantitative measures derived from scans problematic. Similarly, variation in scan signal strength for different individuals complicates the interpretation of quantitative measurements and comparison to population data. In the case of OCT angiography, where decorrelation (flow) values have an underlying dependence on the reflectance signal strength of the OCT scan, variation in OCT reflectance signal strength has a detrimental impact on quantification metrics for structural measurements. For example, such signal strength variation introduces noise into the measurement of decorrelation values that characterize blood flow, and thereby negatively impacts quantification of vessel density, vessel area, avascular area, and other vessel measurements derived therefrom. When using a fixed threshold value for all pixels of an angiogram, vessel density measurements will be lower in regions where the OCT reflectance signal is weaker due to, for instance, vitreous opacity, pupil edge vignetting, and shadowing artifacts. Similarly, regions with strong reflectance signals have correspondingly higher decorrelation values. The disclosed techniques overcome these problems by compensating for variations in reflectance within a given scan so that decorrelation signals indicative of blood flow are properly discriminated and classified.

Disclosed herein is a dynamic thresholding method that mitigates the detrimental effects of both overall signal strength variation in OCT scans and within-scan variation in signal strength. The method first involves characterization of the relationship between the distribution of reflectance signal strength and decorrelation values. This characterization is based on measurements of reflectance signal strength and decorrelation values taken from scans of an avascular region of the eye. These data are used to establish a statistical model that serves as a dynamic threshold function to determine whether decorrelation values are classified as "flow" or "no flow" based on their corresponding reflectance values. By adjusting the threshold according to reflectance signal strength (as opposed to the standard practice of setting a fixed threshold value), the precision and accuracy of vessel measurements are improved by reducing the noise introduced by signal strength variation, bulk motion, and other sources of scan noise.

Also disclosed herein is a method for processing OCT datasets using the dynamic threshold. Implementation details are provided regarding the processing of OCT datasets to generate en face projection angiogram images amenable to compensation by dynamic thresholding. Specifically, the preferred retinal layers from which to extract data for the en face angiogram is described herein, along with the type of projection (e.g., maximum or mean projection) to be used. An important aspect of the disclosed dynamic thresholding approach is that the within-scan variation of reflectance is compensated for on a pixel-by-pixel basis in en face angiograms, rather than adjusted based on an overall index of scan quality. This approach allows scans over a wide range of signal quality (i.e., both high and low signal strength scans) to be utilized for quantification of vascular characteristics. Further, it obviates the need to re-scan eyes in cases where the overall signal strength is deemed too low or too high, or to omit previously acquired scans from consideration where re-scanning is not an option (e.g., a scan from a previous office visit). Consequently, the enhanced repeatability afforded by the disclosed method improves the ability to track disease progression in a patient and monitor response to treatment.

An aspect of the disclosed method is that it provides improved quantification of OCT angiography results for scans already deemed to be "good quality." For instance, while most studies will use a quality control metric such as a hard SSI cutoff level as an exclusion criterion (SSI is defined below), the quantification of such "good quality" scans (e.g., SSI 50) still suffers from a dependence on SSI. By using the disclosed dynamic thresholding method based on the reflectance data within the structural OCT image, this dependence is reduced. As a result, the improved quantification obtained by the use of the disclosed dynamic thresholding method reduces false positives and negatives due to reflectance signal differences between regions within the same scan or between scans in control and study groups. Consequently, the method allows for more accurate diagnosis and improved ability to monitor longitudinally.

In the following detailed description, reference is made to the accompanying drawings which form a part hereof, and in which are shown by way of illustration embodiments that can be practiced. It is to be understood that other embodiments can be utilized and structural or logical changes can be made without departing from the scope. Therefore, the following detailed description is not to be taken in a limiting sense, and the scope of embodiments is defined by the appended claims and their equivalents.

Various operations can be described as multiple discrete operations in turn, in a manner that can be helpful in understanding embodiments; however, the order of description should not be construed to imply that these operations are order dependent.

The description may use the terms "embodiment" or "embodiments," which may each refer to one or more of the same or different embodiments. Furthermore, the terms "comprising," "including," "having," and the like, as used with respect to embodiments, are synonymous.

In various embodiments, structure and/or flow information of a sample can be obtained using OCT (structure) and OCT angiography (flow) imaging based on the detection of spectral interference. Such imaging can be two-dimensional (2-D) or three-dimensional (3-D), depending on the application. Structural imaging can be of an extended depth range relative to prior art methods, and flow imaging can be performed in real time. One or both of structural imaging and flow imaging as disclosed herein can be enlisted for producing 2-D or 3-D images.

Unless otherwise noted or explained, all technical and scientific terms used herein are used according to conventional usage and have the same meaning as commonly understood by one of ordinary skill in the art which the disclosure belongs. Although methods, systems, and apparatuses/materials similar or equivalent to those described herein can be used in the practice or testing of the present disclosure, suitable methods, systems, and apparatuses/materials are described below.

All publications, patent applications, patents, and other references mentioned herein are incorporated by reference in their entirety. In case of conflict, the present specification, including explanation of terms, will control. In addition, the methods, systems, apparatuses, materials, and examples are illustrative only and not intended to be limiting.

In order to facilitate review of the various embodiments of the disclosure, the following explanation of specific terms is provided:

A-scan: A reflectivity profile that contains information about spatial dimensions and location of structures within an item of interest. An A-scan is an axial scan directed along the optical axis of the OCT device and penetrates the sample being imaged. The A-scan encodes reflectivity information (for example, signal intensity) as a function of depth (z-direction).

B-scan: A cross-sectional tomograph that can be achieved by laterally combining a series of axial depth scans (i.e., A-scans) in the x-direction or y-direction. A B-scan encodes planar cross-sectional information from the sample and is typically presented as an image. Thus, a B-scan can be called a cross sectional image.

Dataset: As used herein, a dataset is an ordered-array representation of stored data values that encodes relative spatial location in row-column-depth (x-y-z axes) format. In the context of OCT, as used herein, a dataset can be conceptualized as a three dimensional array of voxels, each voxel having an associated value (for example, an intensity value or a decorrelation value). An A-scan corresponds to a set of collinear voxels along the depth (z-axis) direction of the dataset; a B-scan is made up of set of adjacent A-scans combined in the row or column (x- or y-axis) directions. Such a B-scan can also be referred to as an image, and its constituent voxels referred to as pixels. A collection of adjacent B-scans can be combined form a 3D volumetric set of voxel data referred to as a 3D image. In the system and methods described herein, the dataset obtained by an OCT scanning device is termed a "structural OCT" dataset whose values can, for example, be complex numbers carrying intensity and phase information. This structural OCT dataset can be used to calculate a corresponding dataset termed an "OCT angiography" dataset of decorrelation values reflecting flow within the imaged sample. There is a correspondence between the voxels of the structural OCT dataset and the OCT angiography dataset. Thus, values from the datasets can be "overlaid" to present composite images of structure and flow (e.g., tissue microstructure and blood flow) or otherwise combined or compared.

En Face angiogram: OCT angiography data can be presented as a projection of the three dimensional dataset onto a single planar image called a 2D en face angiogram. Construction of such an en face angiogram requires the specification of the upper and lower depth extents that enclose the region of interest within the retina OCT scan to be projected onto the angiogram image. These upper and lower depth extents can be specified as the boundaries between different layers of the retina (e.g., the voxels between the inner limiting membrane and outer plexiform layer can be used to generate a 2D en face angiogram of the inner retina). Once generated, the en face angiogram image may be used to quantify various features of the retinal vasculature as described herein. This quantification typically involves the setting of a threshold value to differentiate, for example, the pixels that represent active vasculature from static tissue within the angiogram. These 2D en face angiograms can be interpreted in a manner similar to traditional angiography techniques such as fluorescein angiography (FA) or indocyanine green (ICG) angiography, and are thus well-suited for clinical use. It is also common to generate 2D en face images from structural OCT data in a manner analogous to that used to generate 2D en face angiograms.

OCT angiography offers powerful opportunities for diagnosing vascular diseases and for tracking disease progression or response to treatment. For example, eyes with diabetic retinopathy and glaucoma show a significant decrease in vessel density compared to controls. It is essential that the quantification methods used with OCT angiography, such as vessel density, be both accurate and repeatable. Previous studies have noted that quantitative metrics from OCT can correlate with signal strength. For example, it has been shown that thickness measurements based on structural OCT were correlated to reflectance signal strength, and that the signal quality of OCT scans (as measured by overall signal strength) can be variable for a patient both within a visit and across multiple visits. Because the detection of blood flow in OCT angiography depends on the processing of structural OCT scans to extract flow data, there is a need to compensate for the effects of reflectance variation to ensure that quantitative angiography methods are robust to variations in reflectance signal strength.

An analysis of signal from the foveal avascular zone (FAZ), a noise region that is typically devoid of blood flow, as shown herein, demonstrates that decorrelation and decorrelation noise is positively related to log OCT reflectance. To account for this dependence, information from the FAZ can be used to generate an equation that calculates a dynamic threshold value for flow detection based on reflectance. As disclosed herein, compensating for reflectance variation by using dynamic thresholding reduces the dependence of blood flow classification on reflectance signal strength and results in vessel density quantification that is more reliable, with improved population variation and within-visit repeatability.

It was further observed that the average decorrelation value in blood vessels detected by OCT angiography depends on overall scan quality, even for scans that are deemed to be of sufficient quality for clinical use. In commercial OCT systems, overall quality of a scan is typically described using a machine-specific proprietary scoring system to distill scan reflectance data into a scalar measure of quality. For example, RTVue (Optovue Inc., Fremont, Calif., USA) uses "signal strength index" (SSI) and recommends values ≥45 for macular scans and 35 for retinal scans on a scale from 0-100, Stratus OCT (Carl Zeiss Meditec, Dublin, Calif., USA) uses "signal strength" (SS) and recommends values ≥6 on a scale from 0-10, and Spectralis OCT (Heidelberg Engineering, Heidelberg, Germany) uses a "Q score" and recommends values ≥15 on a scale from 0-40. Using an RTVue system, as disclosed herein, it was observed, for instance, that scans that had lower reflectance signal strength (as measured by SSI) tended to have lower decorrelation values in the blood vessels detected by OCT angiography. This relationship existed both between repeated scans obtained from the same eyes, and also between scans obtained from the same region in different eyes and subjects. Thus, signal strength variation introduces noise into the measurement of decorrelation values, as well as vessel density, vessel area, avascular area, and other vessel measurements.

Generating an Equation to Calculate a Dynamic Threshold

To generate a dynamic thresholding equation to compensate for reflectance-related errors in flow measurements, structural OCT scans are performed for a population of participants having clinically normal retinal structure. The imaged area of the retina should encompass a "noise" region where blood flow is known to be minimal or non-existent. The scans can be acquired over a range of scan quality (as characterized, for instance, by signal strength index (SSI) or other manufacturer-specific scan rating value). In an embodiment, the natural scan quality variation inherent in a set of scans acquired from a population of individuals can provide the range of scan quality required. In an alternate embodiment, the quality of the acquired scans can be modulated by positioning neutral density filters of various ratings in front of the eye of each subject during separate, multiple scan acquisitions to vary scan signal strength and ensure that data is gathered over a range of imaging conditions.

For each of the acquired structural OCT datasets, a corresponding OCT angiography dataset (e.g., decorrelation values) is calculated. This OCT angiography calculation may use any of the existing algorithms to detect flow in a sample such as speckle variance, amplitude decorrelation, or SSADA. When the SSADA approach is used, it is further necessary to up-sample the decorrelation dataset by interpolation so that a one-to-one correspondence between values in the structural OCT and OCT angiography datasets is restored.

The retinal layer depths between which reflectance and decorrelation data are to be analyzed is specified. This specification provides the upper and lower depth extents in the axial scan direction to which analysis is confined for purposes of generating a dynamic threshold equation. In an embodiment, the internal limiting membrane (ILM) and the outer boundary of the inner/outer segment (IS/OS) can be used as the bounding layers. For each structural OCT dataset, a 2D en face reflectance image is generated by projecting the data contained between the specified upper and lower depth extents. In an embodiment, the mean reflectance is used to generate these 2D en face reflectance images. Similarly, for each OCT dataset of decorrelation values, a 2D en face angiogram is generated by projecting the data contained between the specified upper and lower depth extents. In an embodiment, the maximum decorrelation is used to generate these 2D en face OCT angiograms. In alternate embodiments, the reflectance and decorrelation data bounded by the upper and lower depth extents can also be analyzed directly, without reducing data dimensionality by 2D en face projection. Such analysis approaches may require, for instance, application of data processing methods to reduce influence of projection artifacts within the reflectance and decorrelation datasets.

Continuing with the paired 2D en face reflection images and angiograms, the aforementioned "noise" region is specified for analysis. In an embodiment, an exemplary region for this analysis is an area within the foveal avascular zone from a macular scan, for example, a circular region 2 mm to 6 mm in diameter centered at the foveal avascular zone and excluding the foveal reflex.

Pixel statistics are calculated within the "noise" region for the paired 2D en face reflectance images and angiograms. For example, in an embodiment, for each projected reflectance image and angiogram pair, a mean reflectance value, a mean decorrelation value, and associated standard deviation of reflectance and standard deviation of decorrelation can be calculated. These data, calculated for a population of participants, can be used, in an embodiment, to generate curve fits for mean decorrelation as a function of mean reflectance, as well as curve fits for standard deviation of decorrelation as a function of mean reflectance. In further embodiments, the reflectance data can be transformed, for instance by to a logarithmic, natural logarithmic, or other scale, as appropriate to improve curve-fitting.

The curve-fits described above can be combined to define a dynamic threshold equation that can be used to classify angiogram pixel values as "flow" or "no flow" based on their associated (log) reflectance values. In such a dynamic threshold equation, pixel decorrelation values in an angiogram lying "above" the threshold line (for example, for the case of a linear regression line fitted to the data) are classified as blood flow, while those below the line are classified as static tissue or noise. Example 1 below provides an example of generating such a dynamic threshold equation based on a curve of fitted (log) reflectance and decorrelation data combined with the fitted standard deviation curve multiplied by a scaling factor. In embodiments, the dynamic thresholding equation can also include a lower bound of applicability, such that pixel reflectance values below a given floor value are not assigned a decorrelation threshold and thus, the pixels are classified as neither "flow" nor "no flow" (i.e., they are invalid).

In an alternate embodiment, a dynamic thresholding equation can be generated from a scatterplot of decorrelation values as a function of reflectance wherein a curve-fit to the scatterplot data is generated, along with error bounds that statistically describe the goodness-of-fit of the fitted curve within a prescribed confidence interval. The analytic function specifying the upper limit of the prescribed error bound is used as a dynamic threshold function to classify decorrelation values as vasculature versus noise. In embodiments, the error bound equation can be calculated as a confidence interval at a specified percentage (for example, 90-99% CI). Alternatively, the error bound equation can be formulated based statistical measures of variability of the decorrelation data (for example, based on a mean offset and a multiple of the standard deviation of the decorrelation data).

When dynamic thresholding is applied to an OCT angiogram, each pixel's reflectance value in an en face image (or OCT angiography dataset) is used to calculate a corresponding decorrelation threshold value using the dynamic threshold function. If the associated decorrelation at that pixel location exceeds the decorrelation threshold, the pixel is classified as a "flow" or vasculature pixel; otherwise it is categorized as a "no flow" or background noise pixel. This classification scheme can also be applied in an analogous manner to the voxels comprising the associated reflectance and decorrelation dataset, where the reflectance and decorrelation values have not been projected onto a 2D en face plane. In embodiments, a floor threshold can be specified as part of the dynamic threshold equation definition to prevent noise from low reflectance regions being classified as vasculature.

In embodiments, the mathematical form of the dynamic threshold equation may take the form of a continuous linear or non-linear function (e.g., polynomial, power law, exponential), a piecewise or discontinuous function, or other appropriate formulation to represent the underlying data. In one embodiment, the dynamic threshold equation is calculated by first using linear regression to fit the reflectance versus decorrelation data, and then determining the equation for the upper 99% confidence interval of the regression line to serve as the dynamic threshold equation. In addition, multivariate models may be used to define the dynamic threshold equation for datasets with more than one dependent variable (for example, SSI, age, or other factors may be incorporated into the regression model).

An important consideration in implementing dynamic thresholding for discriminating vasculature from background noise is choosing which reflectance values to use in the dynamic thresholding equation. When assessing the flow information between ILM and outer boundary of IPL (inner plexiform layer), ideally one would use the reflectance information from the same bounded slab when determining the dynamic threshold. However, the NFL (nerve fiber layer, located just below the ILM) thins peripherally, which induces an artificial gradient in threshold values. In addition, automated NFL segmentation is difficult at the peripheral areas where the thin NFL is difficult to delineate. Thus, in an embodiment, the difficulty of generating accurate NFL segmentation can be avoided by choosing to use reflectance values from the en face image generated by the projection between the outer boundaries of IPL and IS/OS. Using these values directly, however, can result in thresholds that are too high as well. In an embodiment, when the dynamic threshold equation is derived from the FAZ, which has lower reflectance than the retina outside the FAZ, the difference can be offset by subtraction of the average difference between the two regions.

EXAMPLES

The following examples are illustrative of the disclosed method. In light of this disclosure, those skilled in the art will recognize that variations of these examples and other examples of the disclosed method would be possible without undue experimentation.

Example 1—Dynamic Thresholding Equation Generated Using Neutral Density Filters

Study Information for Example 1

This observational study was performed at the Casey Eye Institute. The research protocols were approved by the Institutional Review Board at the Oregon Health & Science University and carried out in accordance with the tenets of the Declaration of Helsinki. Written informed consent was obtained from each participant.

Healthy volunteers were recruited for the study. The inclusion criteria for healthy eyes were as follows: (1) no evidence of retinal pathology or glaucoma; (2) intraocular pressure less than 21 mm Hg; (3) no chronic or systemic corticosteroid use; (4) best-corrected visual acuity less than 20/40; and (5) refractive error between −7 and +3 diopter.

Thirty healthy participants were included in this study. The age of the participants were 65±9 years (average±standard deviation, range: 43-80). Two macular volumetric datasets were collected from single eyes of all participants. Angiography scans were performed on the RTVue-XR Avanti with AngioVue (Optovue, Fremont, Calif.). The macular angiography scan protocol for a single volumetric dataset contained 2 scans covering a 6×6 mm area. Each scan was comprised of 304×304×2 A-scans and was acquired in less than three seconds. The fast scanning direction was in the horizontal direction for the first scan and in the vertical direction for the second. The SSADA algorithm was applied to detect flow by calculating the decorrelation of the OCT reflectance signal between the 2 consecutive B-scans at the same location. The two scans were then registered and merged through an orthogonal registration algorithm to form a single volumetric dataset. The scanning software also computed a signal strength index (SSI) value based on the volumetric OCT reflectance signal. SSI has often been used as an indicator of scan quality, with higher values representing better quality scan data.

Neutral Density Filter to Reduce OCT Reflectance

Multiple macular angiography scans were performed on five additional healthy participants. Each consecutive scan was collected with an absorptive neural density filter of increasing optical density (NEK01, Thorlab, Newton, N.J.) positioned in front of the eye. Optical densities ranging from 0.1 to 0.6 were used. Scans performed with higher optical density filters had lower SSI values reported by the OCT scanning software. These data were used to assess reflectance attenuation.

Segmentation and En Face Presentation

For each dataset, the RTVue-XR outputted a registered, volumetric log reflectance amplitude matrix (structural OCT) and decorrelation matrix (OCT angiography). Because SSADA involves splitting the OCT interferogram which reduces the axial resolution, the OCT angiography data has 1060 voxels in each axial line (depth dimension). The decorrelation data was interpolated to 640 pixels to match the structural OCT data. In the examples presented in this disclosure, reflectance refers to structural OCT information which is expressed as log reflectance amplitude. Anatomic features in the structural OCT reflectance volume were then used to guide semi-automated segmentation of the inner limiting membrane (ILM), outer boundary of the inner plexiform layer (IPL), and the outer boundary of the inner/outer segment (IS/OS). Mean projection of reflectance and maximum projection of decorrelation were used to generate en face views.

Data Analysis

Linear regression was used to assess the relationship between reflectance and decorrelation at the FAZ and between SSI and vessel density using Microsoft Excel (Microsoft, Redmond, Wash.). Vessel density was calculated from the en face decorrelation image (or angiogram) in custom software written in Matlab 2014a (MathWorks, Natick, Mass.). A decorrelation threshold was used to separate vasculature from background noise. The vessel density was defined as the number of pixels above the threshold divided by the total pixels in the region of interest. To compare vessel density calculations with and without compensating for reflectance, the average and population variation were reported. Coefficient of variation (CV) was used to assess population variance and within-visit repeatability.

Results: Analysis of Reflectance and Decorrelation at the FAZ

To assess the relationship between OCT reflectance and decorrelation, the signal from a noise region (i.e., a region with no flow) was examined. En face OCT reflectance images and angiograms were generated by projecting the mean reflectance and maximum decorrelation, respectively, between ILM and the outer boundary of IS/OS. As shown in FIG. 1, the overall reflectance and decorrelation values were lower with lower SSI. Regional changes in reflectance within each image were also observed, and this regional reflectance variation showed an association between higher decorrelation values and higher reflectance.

Figure 2:
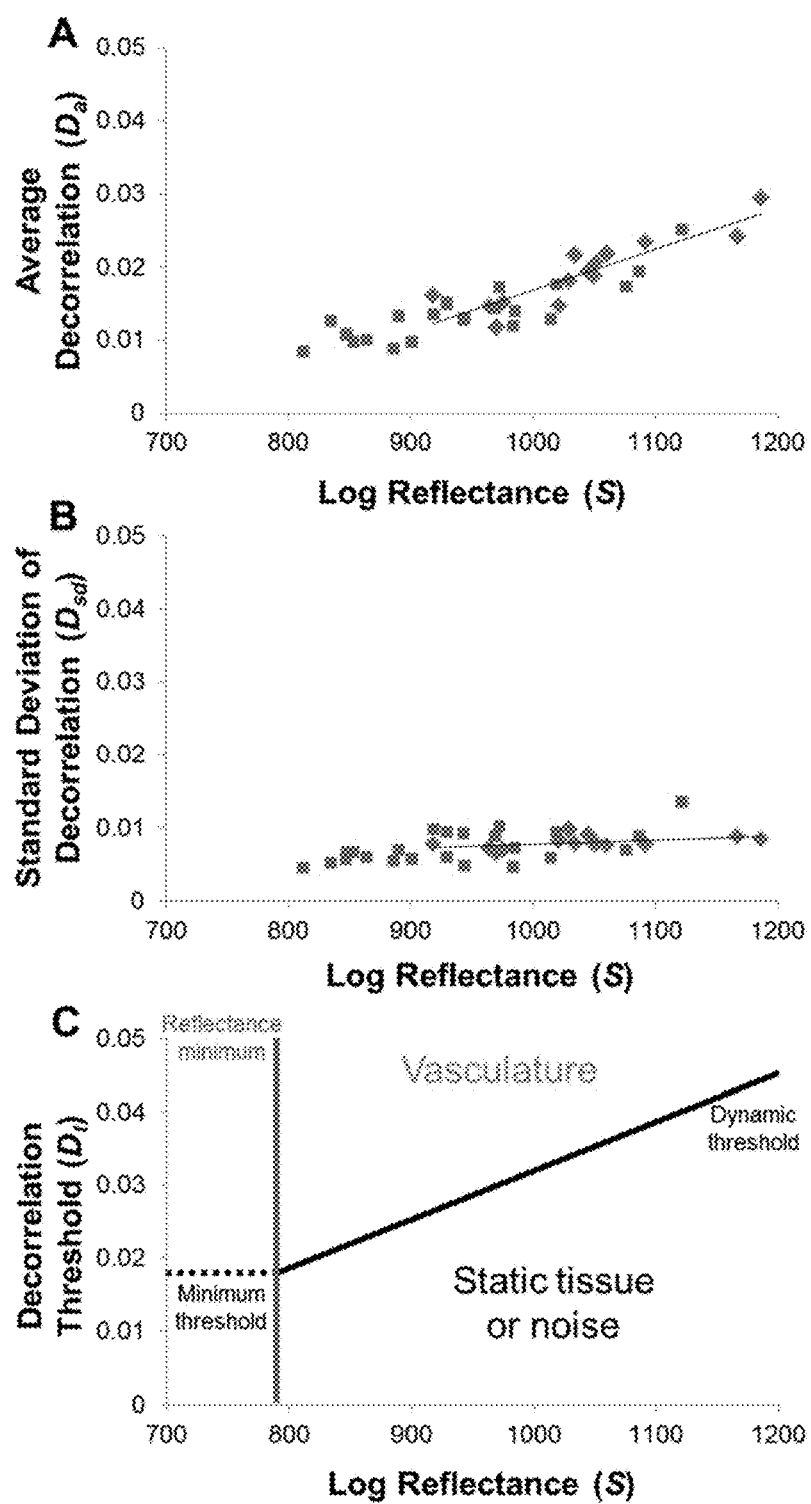
FIG. 2 is a set of three panels depicting the analysis of OCT reflectance and decorrelation at the foveal avascular zone (FAZ) on en face images used to determine a dynamic threshold equation of reflectance compensation. Data marked with diamond shapes were from two datasets of eight participants. Data marked with square shapes were from five participants that received multiple scans with neutral density filters (NDFs) of varying optical densities. (A) Average FAZ decorrelation plotted against average log reflectance from each dataset shoed a positive linear relationship. (B) The standard deviation (SD) of the decorrelation plotted against average log reflectance showed a positive linear relationship. Solid lines show the linear fit of the data from the eight participants, not including any of the data in square shapes. Signal attenuation by NDFs simulated the effect of inter-participant variation well, suggesting that the dependence of background decorrelation on log reflectance was due to OCT beam attenuation in ocular media rather than differences in retinal tissue reflectivity. (C) The fits of the data were used to generate a dynamic decorrelation threshold equation (e.g., Equation 4). Values above the threshold would be considered vasculature while values below would be static tissue or noise. Values to the left of the reflectance minimum were not included in the quantification.

To determine the relationship between OCT reflectance and decorrelation, the signal from a noise region, the FAZ, was analyzed. The datasets from eight of the first ten participants were used; two participants were not included due to the small size of their FAZ or residual motion lines within the FAZ. The SSI of the scans varied from 61 to 78. The FAZ was selected from the en face images, and pixels corresponding to the hyper-reflective foveal reflex when present were identified and removed from the analysis. Analysis of the signal at the FAZ showed a positive linear relationship between log OCT reflectance and OCTA decorrelation as depicted in FIG. 2. The linear fits of the average log reflectance to average decorrelation $D_a$ (FIG. 2A) and standard deviation of the decorrelation $D_{sd}$ (FIG. 2B) were $$D_a = (5.60 \times 10^{-5})S - 0.0391 \quad (1)$$

and $$D_{sd} = (5.58 \times 10^{-6})S + 0.00215 \quad (2)$$

where S is the log amplitude reflectance signal from the RTVue-XR. The relationship between the reflectance amplitude R and the RTVue-XR signal S, as described in (Zhang M et al, *Biomed Opt Express* 7, 806-828 (2016); incorporated by reference herein) was found to be $$R = 6.88 \times 10^{-7} \times 10^{\frac{S}{800}} \quad (3)$$

Equations 1 and 2 were used to generate the following dynamic threshold equation:

$$D_t = (6.69 \times 10^{-5})(S - S_{offset}) - 0.035 \; [\text{Minimum}(S - S_{offset}) = 787] \quad (4)$$

where $D_t$ is the decorrelation threshold. This dynamic threshold equation was set at the average (Equation 1) plus 1.96 times the standard deviation (Equation 2), representing the 97.5 percentile point assuming a normal distribution. A fixed threshold defined using the same data and 97.5 percentile criterion gave decorrelation of 0.0347. In Equation 4, $S_{offset}$ was used to account for the reflectance difference between the regions used for compensation and the region where the dynamic threshold equation was derived. $S_{offset}$ was the average reflectance of the region of interest (specifically, reflectance outside of the 0.6 mm diameter disc centered at the FAZ for macular scans) minus the average reflectance within a 0.3 mm diameter disc centered at the FAZ (1067.1) in the 16 datasets from 8 participants used to derive Equations 1 and 2.

As shown in FIG. 2, signal attenuation by NDFs approximated the effect of inter-individual variation (FIGS. 2A and 2B). This data indicates that the dependence of background decorrelation on log reflectance is likely due to OCT beam attenuation in ocular media rather than differences in retinal tissue reflectivity. Furthermore, $D_a$ is shown to reach a minimum below an S of approximately 900. To prevent the linear dynamic threshold from counting decorrelation signal in extremely low reflectance regions as vasculature, a minimum reflectance threshold was set as shown in FIG. 2C. A value of mean plus 1.28 times the standard deviation, 90% percentile point, of the nine NDF data points below an S of ~900 was used to determine a minimum $D_t$. Using Equation 4 with this prescribed minimum $D_t$ gives a reflectance minimum (S−$S_{offset}$) of 787. Pixels with values below the reflectance minimum were considered invalid and not included in quantification. To reduce the amount of pixels corresponding to large retinal vessels from being considered invalid by this criterion, a circular median filter with a radius of 8 pixels (i.e., diameter of 320 µm) was first applied to the reflectance images before dynamic thresholding was performed.

Results: Vessel Density with and without Reflectance Compensation

Figure 3:
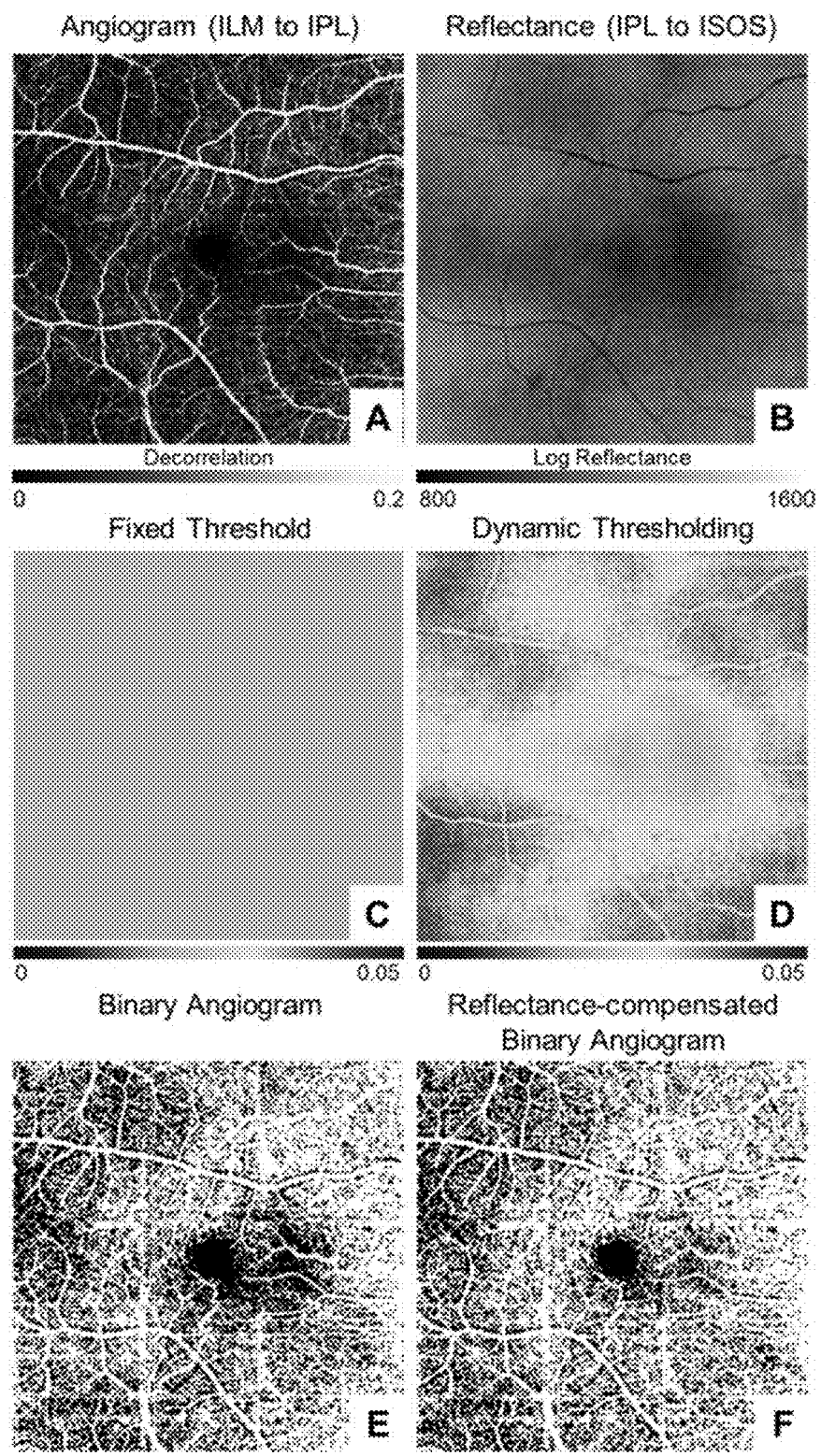
FIG. 3 is a panel of six images that illustrate the improvement in vessel density uniformity using a dynamic threshold compared to a fixed threshold. The images correspond to the macula of a right eye. (A) En face angiogram generated by maximum flow projection in the superficial retinal plexus defined between the inner limiting membrane (ILM) and the outer boundary of the inner plexiform layer (IPL). (B) En face reflectance image generated by the mean log reflectance of the slab between the outer boundaries of IPL and the hyper-reflective inner/outer segment (IS/OS) junction band. (C) Threshold map with a fixed value of 0.0347. (D) Dynamic threshold map derived from the reflectance map shown in Panel B and Equation 4. (E) Binarized image of Panel A based on a fixed threshold for all pixels as shown in Panel C. (F) Binarized image of Panel A based on dynamic thresholding with the values in Panel D. Note the apparent nonperfusion defect in the region immediately nasal to the fovea in Panel E that was improved in Panel F, which compensated for the low reflectance in that area (Panels B, D) likely due to a vitreous opacity. Vessel density is higher on the nasal (disc) side of the image—this is a normal pattern associated with the thicker nerve fiber layer around the optic disc.

The effect of compensating for reflectance in a set of macular scans from thirty participants was studied by comparing quantification of vessel density using either a constant threshold or a dynamic threshold. En face angiograms of the superficial retina were generated by projecting the maximum decorrelation between ILM and the outer boundary of IPL. Vessel density outside of a 0.6 mm diameter disc centered at the FAZ was quantified using a fixed threshold of 0.0347 for all pixels on the angiogram, and using dynamic thresholding which used reflectance information to calculate a threshold based on Equation 4. The reflectance values used to calculate the dynamic threshold were based on the mean projection between the outer boundaries of IPL and IS/OS. Instead of using the reflectance values directly, we first subtracted all values by 64.4 to account for the reflectance difference between the regions used for compensation and where the dynamic threshold equation was derived. Specifically, the 64.4 offset ($S_{offset}$) was the average reflectance outside of the 0.6 mm diameter disc centered at the FAZ (1131.5) minus the average reflectance within a 0.3 mm diameter disc centered at the FAZ (1067.1) in the 16 datasets from 8 participants used to derive Equations 1 and 2. FIG. 3 shows an example case where regional variation in vessel density near the macula was reduced using dynamic thresholding.

Figure 4:
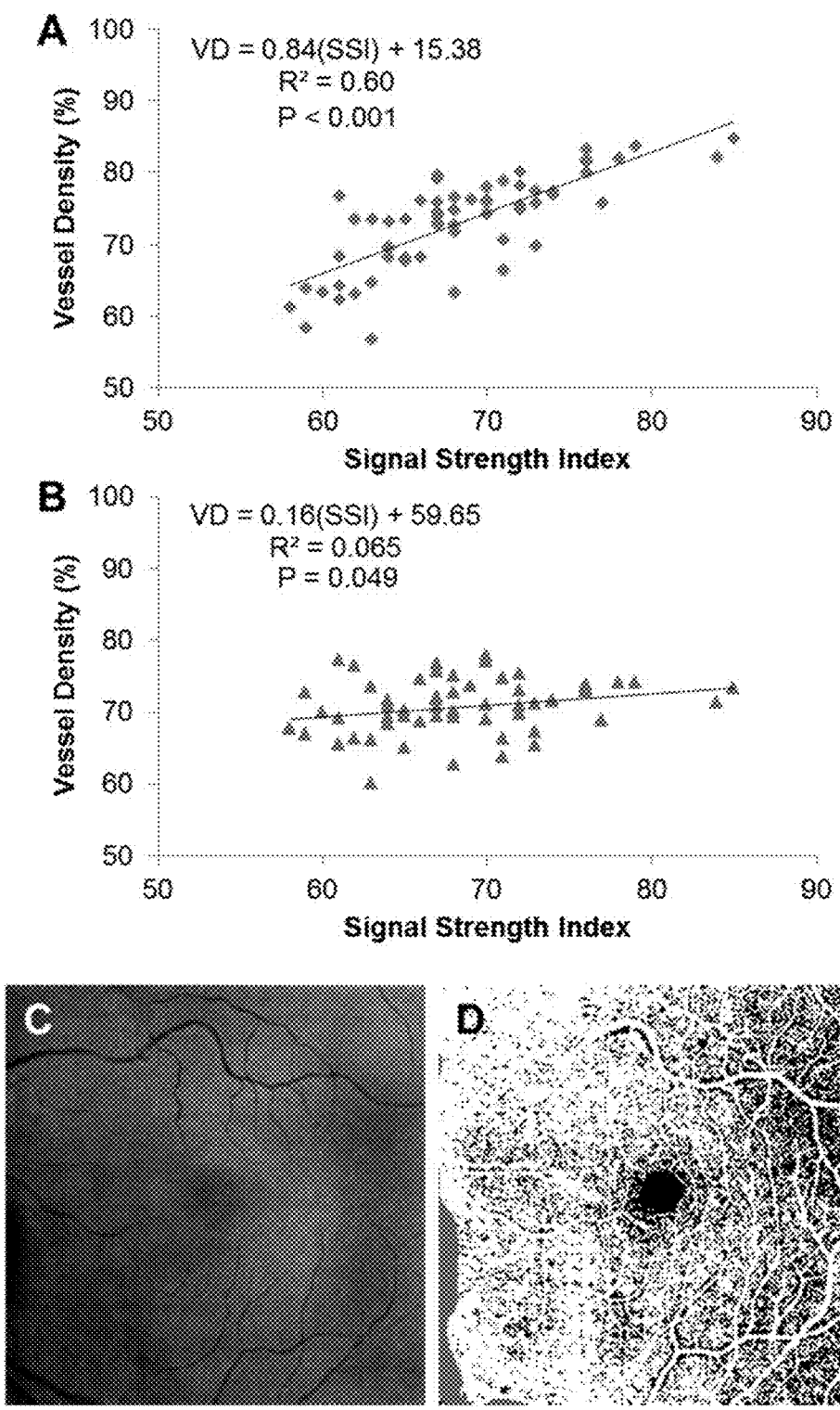
FIG. 4 is a panel of four images that compare the effect of a fixed versus dynamic thresholding approach at the macula. (A) The linear regression when using a fixed threshold had a positive slope, indicating a dependence of measured vessel density on SSI. (B). The linear regression when using dynamic thresholding had a much shallower slope, indicating less dependence of measured vessel density on SSI. For both (A) and (B) the linear fit equation, $R^2$, and P-values are shown on the plots. (C) En face reflectance image of the dataset with the highest percentage of invalid pixels. (D) The reflectance-compensated binary angiogram corresponding to (C) with the invalid pixels marked.

FIG. 4 shows a comparison of the dependence of vessel density on SSI when measured using a fixed threshold approach and a dynamic threshold approach. When using a fixed threshold, the expected positive relationship between SSI and vessel density was observed, as shown in FIG. 4A. The linear regression for the fixed threshold case gave a fit with a slope of 0.84, $R^2$ of 0.60, and a P-value <0.001. When a dynamic threshold was used to assess vessel density, the relationship with SSI was reduced, as shown in FIG. 4B. The linear fit for the dynamic threshold data had a shallower slope of 0.16, $R^2$ of 0.065, and P-value of 0.049. The majority of the cases had less than 1% of the pixels identified as invalid. FIGS. 4C and 4D show the dataset with the highest percentage of invalid pixels (2.2% of pixels). Table 1 shows the average vessel density values, population variation, and within-visit repeatability of the data presented in FIG. 4. Compensating for reflectance variation thus resulted in vessel density quantification with improved population variation and within-visit repeatability.

TABLE 1

Average vessel density, population variation, and within-visit repeatability from the macula of 30 healthy participants

|  | Fixed threshold | Dynamic thresholding |
| --- | --- | --- |
| Vessel density (% area) | 73.2 | 70.7 |
| Population variation (%) | 8.9 | 5.4 |
| Coefficient of variation (%) | 3.9 | 1.6 |

Each participant had 2 datasets.
Population variation and within-visit repeatability were assessed by coefficient of variation.

Example 2—OCT Angiography Image Processing System with Dynamic Thresholding

Figure 5:
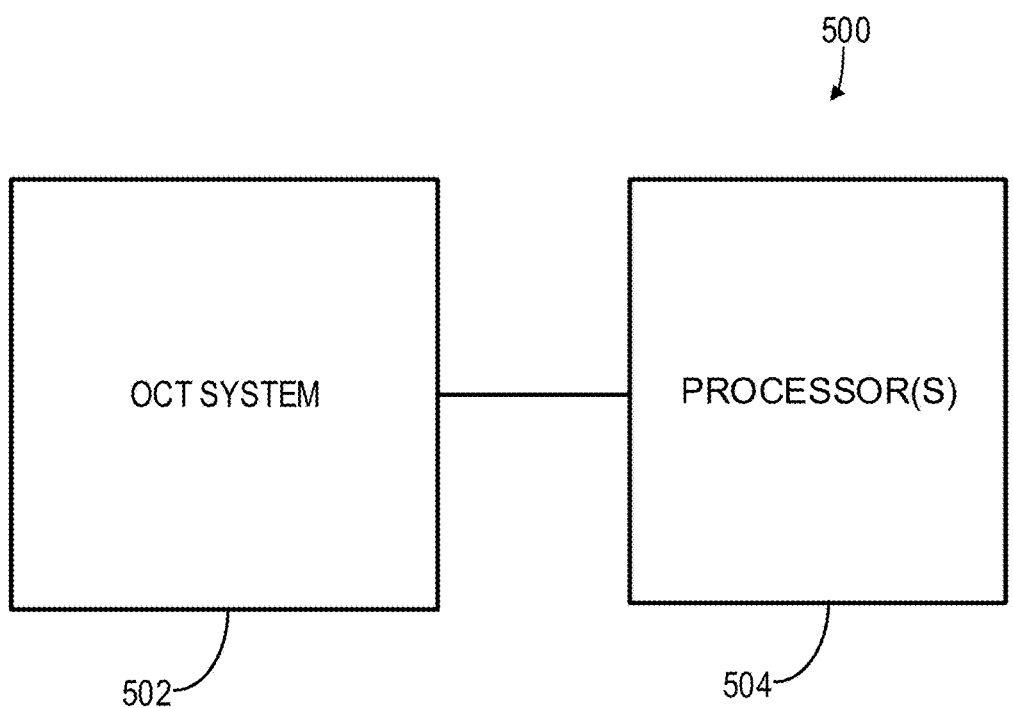
FIG. 5 schematically shows an example system for processing OCT datasets to remove variation in OCT angiography datasets in accordance with the disclosure.

FIG. 5 schematically shows an example system 500 for OCT angiography image processing in accordance with various embodiments. System 500 comprises an OCT system 502 configured to acquire an OCT image comprising OCT interferograms and one or more processors or computing systems 504 that are configured to implement the various processing routines described herein. OCT system 500 may comprise an OCT system suitable for OCT angiography applications, e.g., a swept source OCT system or spectral domain OCT system.

In various embodiments, an OCT system may be adapted to allow an operator to perform various tasks. For example, an OCT system may be adapted to allow an operator to configure and/or launch various ones of the herein described methods. In some embodiments, an OCT system may be adapted to generate, or cause to be generated, reports of various information including, for example, reports of the results of scans run on a sample.

In embodiments of OCT systems comprising a display device, data and/or other information may be displayed for an operator. In embodiments, a display device may be adapted to receive an input (e.g., by a touch screen, actuation of an icon, manipulation of an input device such as a joystick or knob, etc.) and the input may, in some cases, be communicated (actively and/or passively) to one or more processors. In various embodiments, data and/or information may be displayed, and an operator may input information in response thereto.

In some embodiments, the above described methods and processes may be tied to a computing system, including one or more computers. In particular, the methods and processes described herein may be implemented as a computer application, computer service, computer API, computer library, and/or other computer program product.

Figure 6:
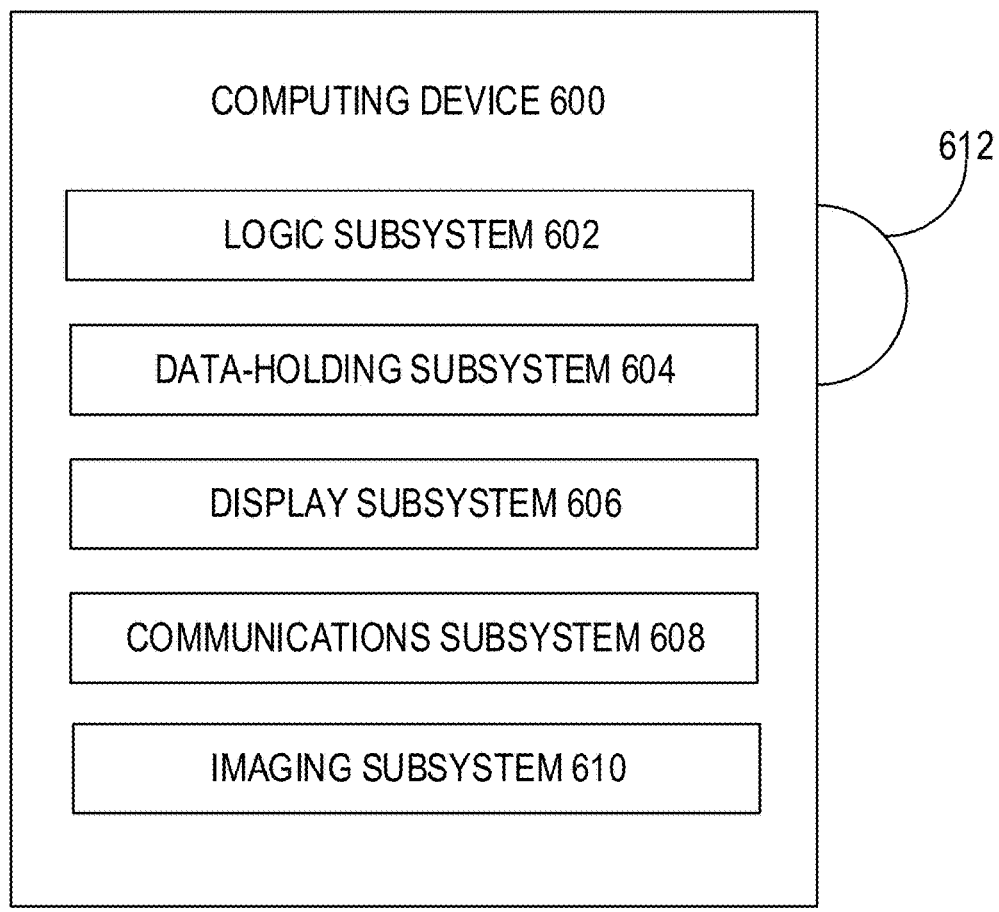
FIG. 6 schematically shows an example of a computing system in accordance with the disclosure.

FIG. 6 schematically shows a non-limiting computing device 600 that may perform one or more of the above described methods and processes. For example, computing device 600 may represent a processor included in system 500 described above, and may be operatively coupled to, in communication with, or included in an OCT system or OCT image acquisition apparatus. Computing device 600 is shown in simplified form. It is to be understood that virtually any computer architecture may be used without departing from the scope of this disclosure. In different embodiments, computing device 600 may take the form of a microcomputer, an integrated computer circuit, printed circuit board (PCB), microchip, a mainframe computer, server computer, desktop computer, laptop computer, tablet computer, home entertainment computer, network computing device, mobile computing device, mobile communication device, gaming device, etc.

Computing device 600 includes a logic subsystem 602 and a data-holding subsystem 604. Computing device 600 may optionally include a display subsystem 606, a communication subsystem 608, an imaging subsystem 610, and/or other components not shown in FIG. 6. Computing device 600 may also optionally include user input devices such as manually actuated buttons, switches, keyboards, mice, game controllers, cameras, microphones, and/or touch screens, for example.

Logic subsystem 602 may include one or more physical devices configured to execute one or more machine-readable instructions. For example, the logic subsystem may be configured to execute one or more instructions that are part of one or more applications, services, programs, routines, libraries, objects, components, data structures, or other logical constructs. Such instructions may be implemented to perform a task, implement a data type, transform the state of one or more devices, or otherwise arrive at a desired result.

The logic subsystem may include one or more processors that are configured to execute software instructions. For example, the one or more processors may comprise physical circuitry programmed to perform various acts described herein. Additionally or alternatively, the logic subsystem may include one or more hardware or firmware logic machines configured to execute hardware or firmware instructions. Processors of the logic subsystem may be single core or multicore, and the programs executed thereon may be configured for parallel or distributed processing. The logic subsystem may optionally include individual components that are distributed throughout two or more devices, which may be remotely located and/or configured for coordinated processing. One or more aspects of the logic subsystem may be virtualized and executed by remotely accessible networked computing devices configured in a cloud computing configuration.

Data-holding subsystem 604 may include one or more physical, non-transitory, devices configured to hold data and/or instructions executable by the logic subsystem to implement the herein described methods and processes. When such methods and processes are implemented, the state of data-holding subsystem 604 may be transformed (e.g., to hold different data).

Data-holding subsystem 604 may include removable media and/or built-in devices. Data-holding subsystem 604 may include optical memory devices (e.g., CD, DVD, HD-DVD, Blu-Ray Disc, etc.), semiconductor memory devices (e.g., RAM, EPROM, EEPROM, etc.) and/or magnetic memory devices (e.g., hard disk drive, floppy disk drive, tape drive, MRAM, etc.), among others. Data-holding subsystem 604 may include devices with one or more of the following characteristics: volatile, nonvolatile, dynamic, static, read/write, read-only, random access, sequential access, location addressable, file addressable, and content addressable. In some embodiments, logic subsystem 602 and data-holding subsystem 604 may be integrated into one or more common devices, such as an application specific integrated circuit or a system on a chip.

FIG. 6 also shows an aspect of the data-holding subsystem in the form of removable computer-readable storage media 612, which may be used to store and/or transfer data and/or instructions executable to implement the herein described methods and processes. Removable computer-readable storage media 612 may take the form of CDs, DVDs, HD- DVDs, Blu-Ray Discs, EEPROMs, flash memory cards, USB storage devices, and/or floppy disks, among others.

When included, display subsystem 606 may be used to present a visual representation of data held by data-holding subsystem 604. As the herein described methods and processes change the data held by the data-holding subsystem, and thus transform the state of the data-holding subsystem, the state of display subsystem 606 may likewise be transformed to visually represent changes in the underlying data. Display subsystem 606 may include one or more display devices utilizing virtually any type of technology. Such display devices may be combined with logic subsystem 602 and/or data-holding subsystem 604 in a shared enclosure, or such display devices may be peripheral display devices.

When included, communication subsystem 608 may be configured to communicatively couple computing device 600 with one or more other computing devices. Communication subsystem 608 may include wired and/or wireless communication devices compatible with one or more different communication protocols. As non-limiting examples, the communication subsystem may be configured for communication via a wireless telephone network, a wireless local area network, a wired local area network, a wireless wide area network, a wired wide area network, etc. In some embodiments, the communication subsystem may allow computing device 600 to send and/or receive messages to and/or from other devices via a network such as the Internet.

When included, imaging subsystem 610 may be used acquire and/or process any suitable image data from various sensors or imaging devices in communication with computing device 600. For example, imaging subsystem 610 may be configured to acquire OCT image data, e.g., interferograms, as part of an OCT system, e.g., OCT system 502 described above. Imaging subsystem 610 may be combined with logic subsystem 602 and/or data-holding subsystem 604 in a shared enclosure, or such imaging subsystems may comprise periphery imaging devices. Data received from the imaging subsystem may be held by data-holding subsystem 604 and/or removable computer-readable storage media 612, for example.

It is to be understood that the configurations and/or approaches described herein are exemplary in nature, and that these specific embodiments or examples are not to be considered in a limiting sense, because numerous variations are possible. The specific routines or methods described herein can represent one or more of any number of processing strategies. As such, various acts illustrated can be performed in the sequence illustrated, in other sequences, in parallel, or in some cases omitted. Likewise, the order of the above-described processes can be changed.

The subject matter of the present disclosure includes all novel and nonobvious combinations and subcombinations of the various processes, systems and configurations, and other features, functions, acts, and/or properties disclosed herein, as well as any and all equivalents thereof.

The invention claimed is:

1. A method of compensating for the effect of tissue reflectance in optical coherence tomography (OCT) angiography, the method comprising:
   receiving a structural OCT dataset;
   obtaining an OCT decorrelation dataset;
   delineating a first retinal layer boundary in the structural OCT dataset;
   delineating a second retinal layer boundary in the structural OCT dataset;
   delineating a third retinal layer boundary in the structural OCT dataset;
   generating an en face angiogram from the data between the first retinal layer boundary and the second retinal layer boundary in the OCT decorrelation dataset, the en face angiogram including a plurality of pixels;
   generating an en face reflectance image from the data between the second retinal layer boundary and the third retinal layer boundary in the structural OCT dataset, the en face reflectance image including a plurality of pixels;
   for individual pixels in the en face reflectance image:
      calculating a dynamic threshold value based on the pixel's reflectance value;
      classifying a corresponding pixel in the en face angiogram as "flow," provided that the pixel's decorrelation value is greater than the dynamic threshold value;
      classifying the corresponding pixel in the en face angiogram as "no flow," provided that the pixel's decorrelation value is less than the dynamic threshold value; and
   returning a reflectance-compensated decorrelation image.

2. The method of claim 1, wherein the first retinal layer boundary is the inner limiting membrane.

3. The method of claim 1, wherein the second retinal layer boundary is the outer boundary of the inner plexiform layer.

4. The method of claim 1, wherein the third retinal layer boundary is the outer boundary of inner/outer segment.

5. The method of claim 1, wherein generating the en face angiogram comprises calculating a maximum projection.

6. The method of claim 1, wherein generating the en face reflectance image comprises performing a mean projection.

7. The method of claim 1, further comprising interpolating the OCT decorrelation dataset to the same size as the structural OCT dataset.

8. The method of claim 1, wherein calculating a dynamic threshold value based on the pixel's reflectance value comprises using:

$$D_t = (6.69 \times 10^{-5})(S - S_{offset}) - 0.035 \text{ [Minimum}(S - S_{offset}) = 787]$$

where $D_t$ is the decorrelation threshold, S is a decorrelation signal associated with the OCT decorrelation dataset, and $S_{offset}$ is an offset value to account for the reflectance difference between regions used for compensation and a region where the dynamic threshold equation was derived.

9. A method of compensating for the effect of tissue reflectance in optical coherence tomography (OCT) angiography, the method comprising:
   receiving a structural OCT dataset;
   obtaining an OCT decorrelation dataset;
   generating an en face angiogram from the OCT decorrelation dataset, the en face angiogram including a plurality of pixels;
   generating an en face reflectance image from the structural OCT dataset, the en face reflectance image including a plurality of pixels;
   for individual pixels in the en face reflectance image:
      calculating a dynamic threshold value based on the pixel's reflectance value;
      classifying a corresponding pixel in the en face angiogram as "flow," provided that the pixel's decorrelation value is greater than the dynamic threshold value;
      classifying the corresponding pixel in the en face angiogram as "no flow," provided that the pixel's decorrelation value is less than the dynamic threshold value; and returning a reflectance-compensated decorrelation image;
wherein calculating a dynamic threshold value based on the pixel's reflectance value comprises using:

$$D_t = (6.69 \times 10^{-5})(S - S_{offset}) - 0.035 \text{ [Minimum}(S - S_{offset}) = 787]$$

where $D_t$ is the decorrelation threshold, S is a decorrelation signal associated with the OCT decorrelation dataset, and $S_{offset}$ is an offset value to account for the reflectance difference between regions used for compensation and a region where the dynamic threshold equation was derived.

10. The method of claim 9, wherein generating the en face angiogram comprises calculating a maximum projection.

11. The method of claim 9, wherein generating the en face reflectance image comprises performing a mean projection.

12. The method of claim 9, further comprising:
    delineating a first retinal layer boundary in the structural OCT dataset, wherein the first retinal layer boundary is the inner limiting membrane;
    delineating a second retinal layer boundary in the structural OCT dataset, wherein the second retinal layer boundary is the outer boundary of the inner plexiform layer; and
    delineating a third retinal layer boundary in the structural OCT dataset, wherein the third retinal layer boundary is the outer boundary of inner/outer segment;
    wherein the generating the en face angiogram from the OCT decorrelation dataset corresponds to generating the en face angiogram from the data between the first retinal layer boundary and the second retinal layer boundary in the OCT decorrelation dataset; and
    wherein the generating the en face reflectance image from the structural OCT dataset corresponds to generating the en face reflectance image from the data between the second retinal layer boundary and the third retinal layer boundary in the structural OCT dataset.

13. A system comprising:
    an OCT system to acquire a structural optical coherence tomography (OCT) dataset and an OCT decorrelation dataset;
    a logic subsystem; and
    a data holding subsystem comprising machine-readable instructions stored thereon that are executable by the logic subsystem to:
        delineate a first retinal layer boundary, a second retinal layer boundary, and a third retinal layer boundary in the structural OCT dataset;
        generate an en face angiogram from the data between the first retinal layer boundary and the second retinal layer boundary in the OCT decorrelation dataset, the en face angiogram including a plurality of pixels;
        generate an en face reflectance image from the data between the second retinal layer boundary and the third retinal layer boundary in the structural OCT dataset, the en face reflectance image including a plurality of pixels;
        determine a dynamic threshold value for individual pixels in the en face reflectance image;
        classify the individual pixels as flow or no flow based on the respective dynamic threshold value; and
        generate a flow image based on the classified pixels.

14. The system of claim 13, wherein the first retinal layer boundary is the inner limiting membrane.

15. The system of claim 13, wherein the second retinal layer boundary is the outer boundary of the inner plexiform layer.

16. The system of claim 13, wherein the third retinal layer boundary is the outer boundary of inner/outer segment.

17. The system of claim 13, wherein, to generate the en face angiogram, the instructions are executable by the logic subsystem to calculate a maximum projection.

18. The system of claim 13, wherein to generate the en face reflectance image, the instructions are executable by the logic subsystem to perform a mean projection.

19. The system of claim 13, wherein the instructions are further executable by the logic subsystem to interpolate the OCT decorrelation dataset to the same size as the structural OCT dataset.

20. The system of claim 13, wherein the dynamic threshold value is determined based on the pixel's reflectance value according to:

$$D_t = (6.69 \times 10^{-5})(S - S_{offset}) - 0.035 \text{ [Minimum}(S - S_{offset}) = 787]$$

where $D_t$ is the decorrelation threshold, S is a decorrelation signal associated with the OCT decorrelation dataset, and $S_{offset}$ is an offset value to account for the reflectance difference between regions used for compensation and a region where the dynamic threshold equation was derived.

* * * * *